United States Patent
Wachter et al.

(10) Patent No.: US 12,133,840 B2
(45) Date of Patent: Nov. 5, 2024

(54) HALOGENATED XANTHENE COMPOSITION AND METHOD FOR TREATING HEMATOLOGIC CANCERS

(71) Applicants: Provectus Pharmatech, Inc., Knoxville, TN (US); UTI Limited Partnership, Calgary (CA)

(72) Inventors: Eric A. Wachter, Oak Ridge, TN (US); Dominic Rodrigues, Knoxville, TN (US); Satbir Thakur, Calgary (CA); Lucy Swift, Calgary (CA); Chunfen Zhang, Calgary (CA); Mohit Jain, Calgary (CA); Aru Narendran, Calgary (CA)

(73) Assignees: Provectus Pharmatech, Inc., Knoxville, TN (US); UTI Limited Partnership, Calgary (CA)

(*) Notice: Subject to any disclaimer, the term of this patent is extended or adjusted under 35 U.S.C. 154(b) by 258 days.

(21) Appl. No.: 17/890,659

(22) Filed: Aug. 18, 2022

(65) Prior Publication Data
US 2024/0082206 A1    Mar. 14, 2024

Related U.S. Application Data

(62) Division of application No. 16/688,319, filed on Nov. 19, 2019, now Pat. No. 11,419,844.

(51) Int. Cl.
| | |
|---|---|
| *A61K 31/352* | (2006.01) |
| *A61K 9/00* | (2006.01) |
| *A61K 31/21* | (2006.01) |
| *A61P 35/00* | (2006.01) |
| *C07K 16/28* | (2006.01) |

(52) U.S. Cl.
CPC .......... *A61K 31/352* (2013.01); *A61K 9/0019* (2013.01); *A61K 31/21* (2013.01); *A61P 35/00* (2018.01); *C07K 16/2818* (2013.01); *C07K 16/2827* (2013.01); *C07K 16/2875* (2013.01)

(58) Field of Classification Search
CPC ............ A61K 2300/00; A61K 31/4035; A61K 31/519; A61K 31/522; A61K 31/352; A61K 45/06; A61K 9/0019; A61K 9/0053; A61K 9/08; A61K 9/167; A61P 35/00; A61P 35/02; C07K 16/2818; C07K 16/2827; C07K 16/2875
See application file for complete search history.

(56) References Cited

U.S. PATENT DOCUMENTS

| | | | |
|---|---|---|---|
| 5,998,597 A | 12/1999 | Fisher et al. | |
| 6,331,286 B1 | 12/2001 | Dees et al. | |
| 6,493,570 B1 | 12/2002 | Dees et al. | |
| 7,390,668 B2 | 6/2008 | Dees et al. | |
| 7,648,695 B2 | 1/2010 | Dees et al. | |
| 8,974,363 B2 | 3/2015 | Dees et al. | |
| 9,107,887 B2 | 8/2015 | Eagle et al. | |
| 9,808,524 B2 | 11/2017 | Eagle et al. | |
| 9,839,688 B2 | 12/2017 | Eagle et al. | |
| 10,130,658 B2 | 11/2018 | Singer et al. | |
| 10,471,144 B2 | 11/2019 | Eagle et al. | |
| 2003/0133940 A1 | 7/2003 | Dees et al. | |
| 2015/0290318 A1 | 10/2015 | Eagle et al. | |
| 2019/0185567 A1 | 6/2019 | Martin et al. | |

OTHER PUBLICATIONS

Saletta, F. et al, "Advances in Paediatric Cancer," Translational Pediatrics, vol. 3, No. 2, 2014, pp. 156-182.
Inaba, H. et al, "Phase I Pharmacokinetic and Pharmacodynamic Study of the Multikinase Inhibitor Sorafenib in Combination with Clofarabine and Cytarabine in Pediatric Relapsed/Refractory Leukemia," Journal of Clinical Oncology, vol. 29, No. 24, Aug. 20, 2011, pp. 3293-3300.
Zwaan, C.M. et al, "Salvage Treatment for Children with Refractory First or Second Relapse of Acute Myeloid Leukaemia with Gemtuzumab Ozogamicin: Results of a Phase II Study," British Journal of Haematology, vol. 148, Dec. 8, 2009, pp. 768-776.
Windebank, K. et al, "Post Cardiac Transplantation Lymphoproliferative Disorder Presenting as t(8;14) Burkitt Leukaemia/Lymphomia Treated with Low Intensity Chemotherapy and Rituximab," Pediatric Blood & Cancer, vol. 53, 2009, pp. 392-396.
Gross, T.G. et al, "Low-Dose Chemotherapy and Rituximab for Post-Transplant Lymphoproliferative Disease (PTLD): A Children's Oncology Group Report," American Journal of Transplantation, vol. 12, No. 11, Nov. 2012, pp. 3069-3075.
Pro, B. et al, "Brentuximab Vedotin (SGN-35) in Patients with Relapsed or Refractory Systemic Anaplastic Large-Cell Lymphoma: Results of a Phase II Study," Journal of Clinical Oncology, vol. 30, No. 18, Jun. 20, 2012, pp. 2190-2196.
Mosse, Y.P. et al, "Safety and Activity of Crizotinib for Paediatric Patients with Refractory Solid Tumours or Anaplastic Large-Cell Lymphoma: A Children's Oncology Group Phase 1 Consortium Study," Lancet Oncology, vol. 14, No. 6, May 2013, pp. 472-480.
Basel, M.T. et al, "Developing a Xenograft Human Tumor Model in Immunocompetent Mice," Cancer Letters, vol. 412, 2018, pp. 256-263.

(Continued)

*Primary Examiner* — Savitha M Rao
(74) *Attorney, Agent, or Firm* — Husch Blackwell LLP

(57) ABSTRACT

A method of treating a mammalian subject having hematologic, non-tumorous cancer cells is disclosed. The method comprises the steps of: (A) administering to such a mammalian subject a therapeutically effective amount of a halogenated xanthene, a pharmaceutically acceptable salt or a $C_1$-$C_4$ alkyl ester thereof as a first cancer cytotoxic agent dissolved or dispersed in a pharmaceutically acceptable aqueous medium. The mammalian subject is maintained for a period of time sufficient to induce death of hematologic, non-tumorous cancer cells. A contemplated administration is typically repeated. A contemplated treatment method can also be carried out in conjunction with administration to said mammalian subject of a second therapeutically effective amount of a second, differently-acting cancer cytotoxic agent dissolved or dispersed in a pharmaceutically acceptable medium. The second cancer cytotoxic agent can be a small molecule or an intact antibody or paratope-containing portion thereof.

15 Claims, No Drawings

(56) References Cited

OTHER PUBLICATIONS

Yvart, J. et al, "I Rose Bengal: Its Use in the Evaluation of Infantile Jaundice," European Journal of Nuclear Medicine, vol. 6, 1981, pp. 355-359.

Wachter, E. et al, "Functional Imaging of Photosensitizers Using Multiphoton Microscopy," Proceedings of SPIE, Multiphoton Microscopy in the Biomedical Sciences II, vol. 4620, 2002, pp. 143-147.

Qin, Z. et al, "Colon Cancer Cell Treatment with Rose Bengal Generates a Protective Immune Response via Immunogenic Cell Death," Cell Death and Disease, vol. 8, No. 7, Feb. 2, 2017, e2584.

Toomey, P. et al, "Intralesional Injection of Rose Bengal Induces a Systemic Tumor-Specific Immune Response in Murine Models of Melanoma and Breast Cancer," PLoS One, vol. 8, issue 7, Jul. 2013, e68561.

Koevary, S.B., "Selective Toxicity of Rose Bengal to Ovarian Cancer Cells in Vitro," International Journal of Physiology, Pathophysiology and Pharmacology, vol. 4, No. 2, 2012, pp. 99-107.

Thompson, J.F. et al, "Chemoablation of Metastatic Melanoma Using Intralesional Rose Bengal," Melanoma Research, vol. 18, 2008, pp. 405-411.

Zamani, S. et al, "Rose Bengal Suppresses Gastric Cancer Cell Proliferation via Apoptosis and Inhibits Nitric Oxide Formation in Macrophages," Journal of Immunotoxicology, vol. 11, No. 4, 2014 (early online 1-9).

Thompson, J.F. et al, "Phase 2 Study of Intralesional PV-10 in Refractory Metastatic Melanoma," Annals of Surgical Oncology, vol. 22, No. 7, 2015, pp. 2135-2142.

Agarwala, S.S, et al, "Phase 1B Study of PV-10 and Anti-PD-1 in Advanced Cutaneous Melanoma," Journal of Clinical Oncology, vol. 37, No. 15, May 26, 2019, suppl. abstr. 9559.

Swift, L. et al, "Potent in vitro and Xenograft Antitumor Activity of a Novel Agent, PV-10, Against Relapsed and Refractory Neuroblastoma," OncoTargents and Therapy, vol. 12, 2019, pp. 1293-1307.

Foote, M. et al, "Results of a Phase II, Open-Label, Non-Comparative Study of Intralesional PV-10 Followed by Radiotherapy for the Treatment of In-Transit of Metastatic Melanoma," Journal of Surgical Oncology, vol. 115, No. 7, 2017, pp. 891-897.

Liu, H. et al, "Intralesional Rose Bengal in Melanoma Elicits Tumor Immunity via Activation of Dendritic Cells by the Release of High Mobility Group Box 1," Onco Target, vol. 7, No. 25, 2016, pp. 37893-37905.

Lippey, J. et al, "Intralesional PV-10 for In-Transit Melanoma—A Single Center Experience," Journal of Surgical Oncology, vol. 114, 2016, pp. 380-384.

Liu, H. et al, "T Cell Mediated Immunity after Combination Therapy with Intralesional PV-10 and Blockade of the PD-1/PD-L1 Pathway in a Murine Melanoma Model," PLoS One, vol. 13, No. 4, Apr. 25, 2018: e0196033.

Darvin, P. et al, "Immune Checkpoint Inhibitors: Recent Progress and Potential Biomarkers," Experimental and Molecular Medicine, 2018, vol. 50:165.

Berge, S.M. et al, "Pharmaceutical Salts," Journal of Pharmaceutical Sciences, vol. 66, No. 1, Jan. 1977, pp. 1-19.

Howard, S.C. et al, "The Tumor Lysis Syndrome," New England Journal of Medicine, vol. 364, No. 19, May 12, 2011, pp. 1844-1854.

Akbarzadeh, A. et al, "Liposome: Classification, Preparation, and Applications," Nanoscale Research Letters, 2013, vol. 8: 102.

DiJoseph, J.F. et al, "Antibody-Targeted Chemotherapy with CMC-544: a CD22-Targeted Immunoconjugate of Calicheamicin for the Treatment of B-Lymphoid Malignancies," Blood, vol. 103, 2004, pp. 1807-1814.

Francisco, J.A. et al, "cAC10-vcMMAE, an Anti-CD30-Monomethyl Auristatin E Conjugate with Potent and Selective Antitumor Activity," Blood, vol. 102, 2003, pp. 1458-1465.

Dornan, D. et al, "Therapeutic Potential of an Anti-CD79b Antibody-Drug Conjugate, Anti-CD79b-vc-MMAE, for the Treatment of Non-Hodgkin Lymphoma," Blood, vol. 114, No. 13, Sep. 24, 2009, pp. 2721-2729.

Swift, L. et al, "In Vitro Activity and Target Modulation of PV-10 Against Relapsed and Refractory Pediatric Leukemia," Blood, 2018, vol. 132, supp. 1: 5207.

Definition of Hematologic Cancer, National Cancer Institute, NCI Dictionary of Cancer Terms, https://www.cancer.gov/publications/dictionaries/cancer-terms/def/hematologic-cancer; (retrieved from Internet on Jan. 7, 2020).

"Lymphoma," Wikipedia, pp. 1-21, https://www.wikipedia.org/wiki/Lymphoma (retrieved from Internet on Jan. 7, 2020).

Cayman Chemical listing re "CEP-40783," pp. 1-3, https://www.caymanchem.com/product25749/cep-40783 (retrieved from Internet on Jan. 7, 2020).

"Ipilimumab," Wikipedia, pp. 1-11, https://www.wikipedia.org/wiki/Ipilimumab (retrieved from Internet on Jan. 7, 2020).

"Tonicity," Wikipedia, pp. 1-3, https://www.wikipedia.org/wiki/Tonicity#Isotonicity (retrieved from Internet on Jan. 15, 2020).

International Search Report re Application No. PCT/US2019/062184, mailed Jan. 30, 2020.

Written Opinion re Application No. PCT/US2019/062184, mailed Jan. 30, 2020.

Swift, L. et al, "In vitro and Xenograft Ant-Tumor Activity, Target Modulation and Drug Synergy Studies of PV-10 Against Refractory Pediatric Solid Tumors," ASCO 2018 poster, Abstract No. 10557, 2018.

HALOGENATED XANTHENE COMPOSITION AND METHOD FOR TREATING HEMATOLOGIC CANCERS

This application is a divisional of copending U.S. application Ser. No. 16/688,319, filed on Nov. 19, 2019 which is incorporated herein by reference.

FIELD OF THE INVENTION

This invention relates to a therapeutic regimen for treating blood (hematologic) cancers such as leukemia, lymphoma, and multiple myeloma, and particularly effecting such treatments in children.

BACKGROUND ART

An adult human has about 7000 white blood cells per microliter (μL) of blood. Of those white cells, about 65 percent are granulocytes (about 4500/μL), about 30 percent are monocytes (about 2100/μL) and about five percent are lymphocytes (about 350/μL). Geyton, *Textbook of Medical Physiology*, Seventh ed., W. B. Saunders Co., Philadelphia (1986). The above cell numbers are, of course, generalized average values, and granulocyte counts for normal patients; i.e., patients free of disease, typically have granulocyte counts of about 2000 to about 7000 cells/μL.

Chronic myelogenous leukemia (CML), also known as chronic granulocytic leukemia (CGL), is a neoplastic disorder of the hematopoietic stem cell. In its early phases it is characterized by leukocytosis, the presence of increased numbers of immature granulocytes in the peripheral blood, splenomegaly and anemia. These immature granulocytes include basophils, eosinophils, and neutrophils. The immature granulocytes also accumulate in the bone marrow, spleen, liver, and occasionally in other tissues. Patients presenting with this disease characteristically have more than 75,000 white blood cells per microliter (μL), and the count can exceed 500,000/μL.

CML accounts for about 20 percent of all leukemias in the United States. About 15 new cases per million people are reported each year, leading to about 3,000 to 4,000 new cases per year. The disease is rare in humans below age 45, rises rapidly to age 65, and remains high thereafter. The median life span of patients with chronic myelogenous leukemia from the time of diagnosis is approximately four years.

About 60 to 80 percent of patients with CML develop a blast crisis. Blast crisis represents a manifestation of acute leukemia. The presence of certain markers on the blast cells sometimes suggests a lymphold origin of these cells during the blast crisis.

Chemotherapeutic agents used for the treatment of the blast crisis are the same as those used for the treatment of other acute leukemias. For example, cytarabine and daunorubicin, used for the treatment of acute myelocytic leukemia, are used to treat CML blast crisis. Prednisone and vincristine, a therapeutic regime used in the treatment of acute lymphocytic leukemias, is also used to treat CML blast crisis. Nevertheless, these drug therapies of the blast crisis stage of CML are even less successful than are the treatments of other acute leukemias.

Cancer in children is rare with an incidence of 140-155 per million per year (age million per year (age <15 years). This translates to ~1 in 7,000 children is diagnosed with cancer each year. Despite the rarity of cancer, malignant neoplasm is the most common cause of death after accidents in children aged 5 to 14 years, accounting for 23% of mortality. Survival from childhood cancers, many of which were fatal in the pre-chemotherapy era, has increased dramatically from 20-30% in the 1960s to 62% in the 1970s, and more recently to 83%. Saletta et al., *Transl Pediatr* 3(2):156-182 (2014).

Leukemias are the most common childhood cancers, accounting for about 30% of all pediatric (ages 1-14) cancer diagnoses. Acute lymphoblastic leukemia (ALL) accounts for about 25% of childrens' cancers, and acute myeloid leukemia (AML) accounts for the remaining about 5%. Non-hodgkin lymphoma (NHL) and Hodgkin lymphoma account for about 6 and about 4% of childhood cancers, respectively. (Ibid.)

Current treatments for ALL include pegylated aspariginase, liposomal daunorubicin, liposomal annamycin, sphingosomal vincristine and liposomal cytarabine. For AML, current treatments include the use of all-trans-retinoic acid (ATRA), arsenic trioxide, anthracycline combined with ATRA, and idarubicin with high-dose cytarabine. Sorafenib (multikinase inhibitor) in combination with clofarabine and cytarabine has found success in a phase I study [Inaba et al., *J Clin Oncol* 29:3293-3300 (2011)], and a calicheamicin-conjugated CD33 antibody, gemtuzumab ozogamicin, known commercially as Mylotarg®, has shown promise [Zwaan et al., *Br J Haematol* 148:768-776 (2010)].

Unlike adults, in whom non-Hodgkin's lymphoma (NHL) is generally low/intermediate grade, pediatric NHL is frequently high grade. NHL can be classified according to phenotype (B-cell vs. T-cell) and differentiation. It falls into three categories: (I) mature B-cell NHL including Burkitt/Burkitt-like lymphoma and diffuse large B-cell lymphoma (DLBCL); (II) lymphoblastic lymphoma (LL) (mostly precursor T-cell); and (III) anaplastic large cell lymphoma (ALCL) (mature T-cell or null-cell). Burkitt lymphoma (BL) is most common, accounting for one-third of pediatric NHL [Saletta et al., *Transl Pediatr* 3(2):156-182 (2014)].

Rituximab (CD 20 antibody) alone and in conjunction with chemotherapy has been undergoing trials in patients with BL and DLBCL [Windebank et al., *Pediatr Blood Cancer* 53:392-396 (2009); and Gross et al., *Am J Transplant* 12:3069-3075 (2012)]. Brentuximab vedotin a chimer of CD30 antibody and monomethyl auristatin E has shown positive responses and remissions in adult phase II trials [Pro et al., *J Clin Oncol* 30:2190-2196 (2012)], whereas crizotinib and ALK (anaplastic lymphoma kinase) inhibitor elicited positive responses in 8/9 ALCL patients in a phase I study [Masse' et al., *Lancet Oncol* 14:472-480 (2013)].

Hodgkin's lymphoma (HL) is the most common cancer in the 15 to 19 years age group and is four to five times more frequent than in the <15 years age group. HL is typically categorized into classical and nodular lymphocyte predominant HL.

HL was fatal until the 1960s when the MOPP (nitrogen mustard, vincristine, procarbazine and prednisone-containing) chemotherapy regimen was introduced. The cure rate of HL in children has been >90% in the last two decades and is one of the most curable childhood cancers. Unfortunately, survivors of childhood HL are at significant risk of long-term treatment-related morbidity and mortality.

Earlier treatments typically included use of radiation along with chemotherapy, which increased the subsequent finding increased breast cancers in previously treated women. More modern approaches have limited use of radiation in patients in complete response after two cycles of chemotherapy referred to as rapid early responder (RER), omission of involved-field radiation therapy (IFRT) in low risk RER, and gender-based modification of treatment to utilize less gonadal toxic alkylating therapy in males ad avoiding IFRT in females.

Although the survival rate for pediatric leukemia has greatly improved, relapse is a major cause of treatment failure. Approximately 15-20% of pediatric ALL patients and 30-40% of AML patients relapse, with relapsed ALL identified as the fourth most common malignancy in children.

Treatment of relapsed pediatric leukemia includes intensification of chemotherapeutic regimens and use of bone marrow transplantation (BMT). However, increasing the intensity of combination chemotherapies and introduction of second-line drugs is often accompanied by cumulative toxicity with marginal incremental benefits.

A key component for understanding immune system interactions against pediatric cancers is the availability of an applicable animal model. Current xenograft models are limited because they are established in severe combined immunodeficient (SCID) mice and so do not provide information on the contribution of the immune system. Other approaches such as human hematopoietic stem cell reconstitution in immunocompetent animals are cumbersome, expensive and often introduce complex biological variables into the system.

Recently, a novel xenograft tumor model was developed in immunocompetent mice by tolerizing mice fetuses to human tumor cells [Basel et al., *Cancer Lett.* 412:256-263 (2018)]. This model is advantageous because it can be used to better describe the complex interaction between cancerous cells and the immune system through a xenograft technique.

One useful anti-cancer agent group for adult cancerous tumors are the halogenated xanthenes, or the pharmaceutically acceptable salts thereof. See, U.S. Pat. Nos. 6,331,286, 7,390,668, 7,648,695, 9,107,887, 9,808,524, 9,839,688, and 10,130,658. Of those halogenated xanthenes, Rose Bengal disodium, (4,5,6,7-tetrachloro-2',4',5',7'-tetraiodofluorescein disodium; RB) has been found to be particularly effective and easily utilized.

PV-10 is a sterile 10% solution of RB in 0.9% saline that has been used clinically to measure liver function in infants [Yvart et al., *Eur J Nucl Med* 6:355-359 (1981)]. Previous studies have shown that PV-10 accumulates in cancer cell lysosomes [Wachter, et al., *Proceedings of SPIE, Multiphoton Microscopy in the Biomedical Sciences II*, Periasamy, A. and So, P.T.C. (eds), Bellingham, Washington: 4620: 143-147 (2002)] and induces cell death in a range of adult cancers [Qin et al., *Cell Death Dis* 8:e2584 (2017); Toomey et al., *PLoS ONE* 8(7):e68561 (2013); Koevary et al., *Int J Physiol Pathophysiol Pharmacol* 4(2):99-107 (2012); Thompson et al., *Melanoma Res* 18(6):405-411 (2008); and Zamani et al., *J Immunotoxic* 11(4):367-375 (2014)].

PV-10 has been used in a number of clinical trials, both as a single anti-cancer agent and in conjunction with both small molecule and monoclonal antibody anti-cancer agents. Several of those trials are discussed below. Phase I and phase II clinical studies using PV-10 alone as the cytotoxic agent illustratively reported "adverse events were predominantly mild to moderate and locoregional to the treatment site, with no treatment-associated grade 4 or 5 adverse events" [Thompson et al., *Ann Surg Oncol* 22(7):2135-2142 (2015)], and "Treatment-Emergent Adverse Events (TEAEs) were consistent with established patterns for each drug, principally Grade 1-2 injection site reactions attributed to PV-10 and Grade 1-3 immune-mediated reactions attributed to pembrolizumab, with no significant overlap or unexpected toxicities: . . . " [Agarwala et al., *J Clin Oncol* 37(15) suppl 9559-9559 (May 26, 2019)]. It thus appears as though RB is toxic to cancerous cells, but non-toxic to non-cancerous cells.

Because of the often-times very different behavior of adult tumors from pediatric tumors, it was not known whether RB and similar halogenated xanthenes would be effective when used against pediatric cancerous cells, and particularly cancerous hematologic cells. Preliminary in vitro and xenograft studies against neuroblastoma cell lines in cell cultures to which RB was added alone or in conjunction with known anticancer agents, and by intralesional injection in mice, respectively, were reported by one of the present inventors and co-workers to exhibit killing of the cancerous cells. Swift et al., *Oncotargets Ther,* 12:1293-1307 (February 2019).

In addition, intralesional administration of a halogenated xanthene into a tumor provides the active cytotoxic agent directly to the tumor at its highest concentration. In a presently contemplated treatment technique discussed below, administration is often distant from the target cancerous hematiologic cells, thereby possibly diminishing the effectiveness of the cancerocidal halogenated xanthene agent.

However, in a phase II clinical trial for patients with refractory metastatic melanoma, intralesional (IL) injection of PV-10 induced tumor regression with an overall response rate of 51% [Thompson et al., *Ann Surg Oncol* 22(7):2135-2142 (2015)]. PV-10 also demonstrated efficacy in combination with radiotherapy in a phase II clinical trial for patients with in-transit or metastatic melanoma, with an overall response rate of 86.6% [Foote et al., *J Surg Oncol* 115(7): 891-897 (2017)].

In addition to inducing direct cancer cell death, PV-10 has also been shown to induce a tumor-specific immune response in both mouse studies [Qin et al., *Cell Death Dis* 8:e2584 (2017); Toomey et al., *PLoS ONE* 8(7):e68561 (2013); and Liu et al., *Oncotarget* 7(25):37893-37905 (2016)] and human clinical trials [Lippey et al., *J Surg Oncol* 114(3):380-384 (2016); Ross, *J Surg Oncol* 109(4):314-319 (2104); Liu et al., *PLoS ONE* 13(4):e0196033 (2018); and Basel et al., *Cancer Lett* 412:256-263 (2018)]. In murine models of melanoma, treatment with PV-10 induced necrosis of melanoma cells and a localized increase in mononuclear tumor-infiltrating lymphocytes [Lippey et al., *J Surg Oncol* 114(3):380-384 (2016)].

It has been suggested that PV-10-induced immunogenic cell death, releasing tumor antigens to nearby antigen-presenting cells (APCs), facilitated the activating of anti-tumor T and B cells. In a syngeneic murine colon cancer model, injection of cancer cells treated in vitro with PV-10 into mice with the same tumor resulted in slower tumor growth [Qin et al., *Cell Death Dis* 8:e2584 (2017)]. Furthermore, in syngeneic murine melanoma models, combination treatment with intralesional PV-10 and anti-PD1 antibody delayed tumor growth and enhanced T cell activation [Liu et al., *PLoS ONE* 13(4):e0196033 (2108)].

The disclosure below describes the contemplated invention and provides results of studies using halogenated xanthenes such as PV-10 in the treatment of pediatric leukemias.

BRIEF SUMMARY OF THE INVENTION

The present invention contemplates a method of treating a mammalian subject having hematologic, non-tumorous cancer cell. Illustrative hematologic, non-tumorous cancers include leukemia, lymphoma and myeloma. The method comprises the steps of: (A) administering to such a mammalian subject a therapeutically effective amount of a halogenated xanthene, a pharmaceutically acceptable salt or a $C_1$-$C_4$ alkyl ester thereof as a first cancer cytotoxic agent dissolved or dispersed in a pharmaceutically acceptable aqueous medium. The mammalian subject is maintained for a period of time sufficient to induce death of hematologic, non-tumorous cancer cells. A contemplated administration is typically repeated.

A contemplated treatment method can also be carried out in conjunction with administration to that mammalian subject of a second therapeutically effective amount of a second, differently-acting cancer cytotoxic agent dissolved or dispersed in a pharmaceutically acceptable medium. The second cancer cytotoxic agent can be a small molecule or an intact antibody or paratope-containing antibody portion. The first and the second cancer cytotoxic agents can be administered together in the same or different media, or at different times. The second cancer cytotoxic agent can be administered in a solid tablet, capsule, pill or the like or in a liquid medium.

In one aspect, use of a small molecule cancer cytotoxic agent having a molecular weight of about 200 to about 1000 Da is contemplated. Compounds that synergize with a halogenated xanthene such as doxorubicin, etoposide and vincristine are preferred. Intact antibodies or paratope-containing antibody portions are a second group of cancer cytotoxic agents. Preferred among these agents are those referred to as immune check point inhibitors. [See, for example, Darvin et al., *Exp Mol Med*, 50:165 (2018).]

The present invention also contemplates use of a therapeutically effective amount of a halogenated xanthene, a pharmaceutically acceptable salt or a $C_1$-$C_4$ alkyl ester thereof as a first cancer cytotoxic agent dissolved or dispersed in a pharmaceutically acceptable aqueous medium for treatment of a mammalian subject having hematologic, non-tumorous cancer cells, wherein the halogenated xanthene is maintained in the mammalian subject for a period of time sufficient to induce death of hematologic, non-tumorous cancer cells. In a further embodiment, the first cancer cytotoxic agent halogenated xanthene, pharmaceutically acceptable salt or $C_1$-$C_4$ alkyl ester thereof is rose bengal, a pharmaceutically acceptable salt or $C_1$-$C_4$ alkyl ester thereof. In a still further embodiment, the rose bengal is rose bengal disodium salt. Further, the hematologic, non-tumorous cancer cells are leukemia, lymphoma or myeloma. Further, the hematologic, non-tumorous cancer cells, leukemia, lymphoma or myeloma is selected from the group consisting of acute B-cell or T-cell lymphoblastic leukemia, acute myeloid leukemia, non-Hodgkin's lymphoma, and Hodgkin's lymphoma.

DETAILED DESCRIPTION OF PREFERRED EMBODIMENTS

In one aspect, the present invention contemplates a pharmaceutical composition for use in the treatment (killing) of hematologic, non-tumorous cancer cells, e.g., leukemia, lymphoma and myeloma. A contemplated pharmaceutical composition comprises a 0.1% to about 20% (w/v) aqueous medium (as a liquid) of a first cancer cytotoxic agent that is a halogenated xanthene, a physiologically acceptable salt of the halogenated xanthene, or a $C_1$-$C_4$ alkyl ester thereof. A particularly preferred halogenated xanthene salt is rose bengal (4,5,6,7-tetrachloro-2',4',5',7'-tetraiodofluorescein) disodium salt, as is present in PV-10. The composition is administered to provide a therapeutically effective amount of a first cancer cytotoxic agent to a mammal such as a human having a hematologic, non-tumorous cancerous disease such as leukemia, lymphoma and myeloma, or more specifically, acute lymphoblastic leukemia (ALL), acute myeloid leukemia (AML), non-Hodgkin's lymphoma (NHL), or Hodgkin's lymphoma (HL).

The mammalian subject is maintained for a time sufficient to kill hematologic, non-tumorous cancerous cells. The fact and relative amount of cancer killing can be determined by usual means for assaying the status of hematologic, non-tumorous cancers.

The mammalian subject is typically thereafter treated again, usually multiple times. Both the duration of maintenance and the choice to conduct further administrations can depend upon the species of mammal, individual mammalian subjects, the severity of disease, type of disease, age and health of the subject, and the like. These factors are commonly dealt with by physicians skilled in the art of treating hematologic, non-tumorous cancers.

In addition, whereas it is typically desired to rid the body of detectable cancerous cells, that cannot always be done. Sometimes it is sufficient to kill enough cancerous cells to control the disease in stasis, or to reduce the cancerous load of cells so that other therapies can be carried out.

The data provided hereinafter illustrates that the $IC_{50}$ value for use of RB against several leukemia cell lines in vitro is about 50 to about 100 μM. Given that the molecular weight of RB is 1018 g/mole, the above $IC_{50}$ value calculates to about 50 to about 100 mg of RB/liter. It is preferred to achieve that concentration for contacting cancerous cells during an in vivo treatment.

The classic intravenous (IV) diagnostic use of RB was conducted giving 100 mg RB as a single IV dose. In clinical studies of PV-10, RB has been tolerated at 1500 mg delivered IV. The standard adult blood volume is approximately 5 L. Thus, to achieve 100 mg/L in the blood, an adult patient would need to receive approximately 500 mg of RB IV to achieve the $IC_{50}$ value in the bloodstream. Due to the rapid clearance of RB from circulation ($t_{1/2}$ is about 30 minutes), an IV administration would require continuous infusion to maintain peak levels of RB in circulation (i.e., for up to several hours or more).

Administration at the $IC_{50}$ value level would not be toxic to all circulating hematologic, non-tumorous cancerous cells; i.e., only approximately half of cells would be affected at the $IC_{50}$ value. It can therefore be preferred to administer RB at a multiple of the $IC_{50}$ value, up to approximately 1500 mg (i.e., 300 μM).

Alternatively, it can be sufficient to kill only a fraction of the cancerous cells to initiate a functional immune response against remaining tumor burden. The latter case can be preferable to avoid toxic reaction (i.e., so-called "tumor lysis syndrome" due to presence of an abundance of rapidly killed cancer cells. In this situation, the cancer cell debris caused by the cytotoxicity to cancer cells of a halogenated xanthene induces an immune reaction that in turn kills further cancerous hematologic, non-tumorous cells.

The similarly useful halogenated xanthene compounds listed below and their pharmaceutically acceptable salts can have molecular weights that differ from each other by about a factor of three (See, Table 3, U.S. Pat. No. 7,390,688 at columns 15-16). It is preferred that an exact amount of other than RB halogenated xanthene to be used is calculated based on published molecular weights for each such compound and that of RB.

A contemplated halogenated xanthene includes rose bengal (4,5,6,7-tetrachloro-2',4',5',7'-tetraiodofluorescein) that is particularly preferred, erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein. The reader is directed to Berge, *J. Pharm. Sci.* 1977 68(1):1-19 for lists of commonly used pharmaceutically acceptable acids and bases that form pharmaceutically acceptable salts with pharmaceutical compounds.

A $C_1$-$C_4$ alkyl ester of one of the above halogenated xanthene compounds can also be used, with the $C_2$; i.e., ethyl ester, being preferred. Thus, in vitro studies using each of RB, ethyl-Red 3 (erythrosine ethyl ester; 2',4',5',7'-tetraiodofluorescein ethyl ester), 4,5,6,7-tetrabromo-2',4',5',7'-tetraiodofluorescein and ethyl-Pholoxine B (4,5,6,7-tetrachloro-2',4',5',7'-tetrabromofluorescein ethyl ester) exhibited similar anti-tumor activities against CCL-142 renal adenocarcinoma.

A preferred form of rose bengal is rose bengel disodihm that has the structural formula below:

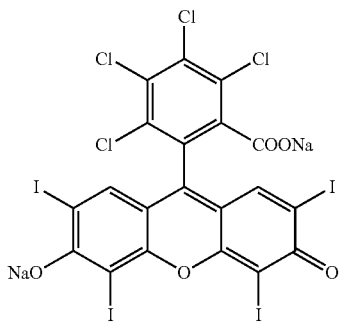

Further details of the medicinal use a pharmaceutical composition containing an above-noted halogenated xanthine are described in U.S. Pat. Nos. 5,998,597, 6,331,286, 6,493,570, 7,390,688, 7,648,695, 8,974,363, 9,107,887, 9,808,524, 9,839,688, 10,130,658 and 10,471,144, whose disclosures are incorporated by reference herein in their entireties.

A contemplated halogenated xanthene or its pharmaceutically acceptable salt is typically used dissolved or dispersed in an aqueous pharmaceutical composition. The halogenated xanthene is typically present at 0.1 to about 20% (w/v) in an aqueous 0.9% saline pharmaceutical composition.

Because a contemplated pharmaceutical composition is typically intended for parenteral administration as by intravenous methods, such a composition should contain an electrolyte, and preferably have approximately physiological osmolality and pH value. A preferred concentration of singly charged electrolyte ions in a pharmaceutically acceptable aqueous medium is about 0.5 to about 1.5% (w/v), more preferably at about 0.8 to about 1.2% (w/v), and most preferably at a concentration of about 0.9% (w/v). The about 0.9% (w/v) concentration is particularly preferred because it corresponds to an approximately isotonic aqueous solution. In a further preferred embodiment, the electrolyte in a chemoablative pharmaceutical composition is sodium chloride.

Electrolytes at such levels increase the osmolality of a pharmaceutically acceptable aqueous medium. Thus, as an alternative to specifying a range of electrolyte concentrations, osmolality can be used to characterize, in part, the electrolyte level of the composition. It is preferred that the osmolality of a composition be greater than about 100 mOsm/kg, more preferably that the osmolality of the composition be greater than about 250 mOsm/kg, and most preferably that it be about 300 to about 500 mOsm/kg.

It is preferred that the pH value of a pharmaceutically acceptable aqueous medium be about 4 to about 9, to yield maximum solubility of the halogenated xanthene in an aqueous vehicle and assure compatibility with biological tissue. A particularly preferred pH value is about 5 to about 8, and more preferably between about 6 to about 7.5. At these pH values, the halogenated xanthenes typically remain in dibasic form, rather than the water-insoluble lactone that forms at low pH values.

The pH value of a pharmaceutically acceptable aqueous medium can be regulated or adjusted by any suitable means known to those of skill in the art. The composition can be buffered or the pH value adjusted by addition of acid or base or the like. As the halogenated xanthenes, or physiologically acceptable salts thereof, are weak acids, depending upon halogenated xanthene concentration and/or electrolyte concentration, the pH value of the composition may not require the use of a buffer and/or pH modifying reagent. It is especially preferred, however, that the composition not contain any buffer, permitting it to conform to the biological environment once administered.

In the present invention, the specific amount of halogenated xanthene in a pharmaceutical composition is not believed to be as important as was the case where the composition was injected intralesionally to a tumor because the object here is to ultimately provide a cytotoxic concentration of halogenated xanthene to the environment of the cancerous cells and in which those cancerous cells can be contacted with the halogenated xanthene. The data provided hereinafter indicate that an $IC_{50}$ concentration of disodium rose bengal is about 50 to about 100 µM for in vitro cultured leukemia cells.

The above results using in vitro cultured leukemia cells surprisingly provided data similar to those obtained in an in vitro cytotoxicity study of cultured SK-N-AS, SK-N-BE(2), IMR5, LAM, SHEP, and SK-N-SH neuroblastoma cells, SK-N-MC neuroepithelioma cells, and normal primary, BJ, and WI38 fibroblasts reported by Swift et. al., *OncoTarqets and Therapy* 12:1-15 (2019). Those authors reported half maximal inhibitory concentration ($IC_{50}$) values for PV-10-treated cells at 96 hours post treatment of 65-85 µM for the neuroblastoma lines assayec, and 49 µM for the neuroepithelioma line SK-N-MC. Those authors also examined toxicity toward human epithelial cells from three tissue sources and reported $IC_{50}$ values of 93-143 µM.

Presuming an $IC_{50}$ value for leukemia cells of about 50 to about 100 µM, a dose to kill about one-half of the leukemia cells in an adult would calculate to be about 50 to about 100 mg of RB/L, based on a molecular weight of 1018 g/mole for disodium RB. The classic IV diagnostic use of RB was conducted giving 100 mg RB as a single IV dose. The standard adult blood volume is approximately 5 L. Thus, to achieve 100 mg/L in the blood, an adult patient would need to receive approximately 500 mg of RB IV to achieve the $IC_{50}$ value in the bloodstream. Intravenous (IV) dosing is a preferred method of administering a halogenated xanthene-containing composition to a mammalian subject in need.

In clinical studies of PV-10, RB has been tolerated at 1500 mg delivered IV. Due to the rapid clearance of RB from circulation ($t_{1/2}$ about 30 minutes) an IV administration would require continuous infusion to maintain peak levels of RB in circulation (i.e., for up to several hours or more) during a single administration.

Administration of sufficient RB to achieve a circulating RB concentration at the $IC_{50}$ level would not be toxic to all circulating leukemic cells (i.e., only approximately half of the leukemic cells would be affected at the $IC_{50}$). In some embodiments it can be preferred to administer RB in an amount that is a multiple of the $IC_{50}$ level, up to approximately 1500 mg (i.e., 300 mM). Alternatively, however, it can be sufficient to kill only a fraction of tumor cells as a result of an individual administration.

The latter case can be preferable for avoiding a toxic reaction (i.e., tumor lysis syndrome) that can result from rapidly killed tumor cell burden. Thus, Howard et al., *N Engl J Med* 364(19):1844-1854 (May 12, 2011) report that tumor lysis syndrome is the most common disease-related emergency encountered by physicians treating hematologic cancers.

A mammal having leukemia, lymphoma or myeloma in need of treatment (a mammalian subject) and to which a pharmaceutical composition containing a halogenated xanthene or its pharmaceutically acceptable salt can be administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

As discussed in greater detail below, it can also be advantageous to kill only a portion of the leukemic cells during a single treatment to initiate a functional immune response against remaining cancer cell burden. A RB-initiated functional immune system response is believed to occur due at least in part from the action of RB-caused necrotic cell debris circulating in the body induces an immune response that can prolong the effects of an initial administration of a halogenated xanthene such as RB.

An induced immune response can take a longer time to develop than the more immediate killing of the contacted cancerous cells. That delay in effect can occur because of the time needed for induction the appropriate B and T cell populations to attack and kill the leukemic cells as well as to induce long lasting memory T cells whose continued circulation can protect the patient from relapse.

In another aspect, an above pharmaceutical composition is used in conjunction with a second, differently-acting cytotoxic anticancer agent; i.e., a cytotoxic anticancer agent whose mechanism of action is different from that of the first cytotoxic agent, the halogenaed xanthene. As noted previously, the halogenated xanthenes localize in cancer cell lysosomes, increase the percentage of cells in G1 phase of the cell cycle and induces cell death by apoptosis [Swift et al., *Oncotargets Ther*, 12:1293-1307 (February 2019)].

A first type of second cytotoxic agent is a so-called "small molecule". Such small molecules can be viewed as semi-specific cellular poisons in that they are generally more specific at killing cancer cells than non-cancerous cells. Almost all small molecule anticancer agents are less cancer-specific than a contemplated halogenated xanthene, and can result in causing sickness, baldness and other trauma to their recipient subjects that can lead to subjects leaving their treatment regimens.

These small molecules typically have molecular weights of about 200 to about 1000 Daltons (Da), and preferably about 250 to about 850 Da. This group of small molecules includes many of the previously noted molecules used to treating hematologic cancers such as calicheamicin (1368 Da), vinblastine (811 Da), vincristine (825 Da), monomethyl auristatin (718 Da), etoposide (589 Da), daunorubicin (528 Da), doxorubicin (544 Da), annamycin (640 Da), sorafenib (465 Da), clofarabine (304 Da), cisplatin (300 Da), irinotecan (587 Da) and cytabarine (243 Da). It is noted that many of these small molecules are used as their salts, prodrugs and/or esters, which consequently have greater molecular weights than those rounded values above.

A pharmaceutical composition having a second cytotoxic anti-cancer agent can also contain a small molecule as above-described that is conjugated to a lager molecule such as a protein, detergent and/or polymer such as poly(ethylene glycol) [PEG]. Such conjugations often minimize the toxicity of the small molecule and enhance situs of delivery as use of an antibody that binds to a cancerous cell. Additionally, a small molecule cytotoxic agent can be enveloped within a liposome, micelle or cyclodextrin molecule that can be adapted to bind specifically bind to cancerous cells and/or be endocytosed by the cancer cell. This group of encapsulated and conjugated small molecules is included with the previously discussed small molecule group of second cytotoxic agents as their active cytotoxic agent is a small molecule.

Illustrative of such second cytotoxic agents are liposomal daunorubicin, liposomal annamycin, sphingosomal vincristine, liposomal cytarabine, a calicheamicin-conjugated CD33 antibody called gemtuzumab ozogamicin and a chimer of CD30 antibody and monomethyl auristatin E called brentuximab vedotin.

Briefly, liposomes are generally spherically-shaped artificial vesicles typically prepared from cholesterol and phospholipid molecules that constitute one or two bilayers and encapsulate the small molecule second cytotoxic agent to assist delivery. See, Akbarzadeh et al., *Nanoscale Res Lett*, 8:102 (2013).

Calicheamicin, is a high molecular weight small molecule (1368 Da), and contains four linked saccharides interrupted by a benzothioate S-ester linkage as well as an ene-diyne group that cleaves DNA sequences. Calicheamicin is too toxic to be used alone, $LD_{50}$ in nude mice of 320 µg/kg [DiJoseph et al., *Blood* 103:1807-1814 (2004)]. Similarly, monomethyl auristatin exhibits general (broad range), high toxicity [$IC_{50}$<1 nM for several cancer cell lines; ApexBio Technology Product Catalog (2013)] that is mediated by linkage to an antibody against CD30 (a TNF receptor-family member that is a cell membrane protein and cancer marker) was reported useful against large cell lymphoma and Hodgkin's disease [Francisco et al., *Blood* 102:1458-1465 (2003)], whereas linkage to an anti-CD79b monoclonal provided an advantage in treating three xenograft models of NHL [Dornan et al., *Blood* 114:2721-2729 (2009)].

A systemic anti-cancer medication that is a small molecule (non-proteinaceous, less than about 1000 grams/mole) or a larger proteinaceous molecule, is administered to the subject mammal to be treated such that the medication spreads throughout the subject's body as compared to the localized administration that occurs with an intralesional administration of a halogenated xanthene. Intravenous administration is a preferred method to achieve that spread of medication.

Illustrative small molecule anti-cancer medications include doxorubicin, etoposide, vincristine, cisplatin, irinotecan and cytarabine that were used herein, whereas an exemplary proteinaceous molecule is egaspargenase. Of those medications, doxorubicin, etoposide and vincristine appeared to synergize with treatment with a sub-lethal dose of PV-10, and are preferred.

It is to be understood that administration of any of the second cancer cytotoxic agents discussed herein can be undertaken multiple times. Such multiple administrations are within the purview of the treating physician, and can be made in conjunction with an administration of a first cancer cytotoxic agent or can be carried out separately.

A useful effective dosage of a small molecule systemic anti-cancer medication is the dosage set out in the labeling information of a FDA-, national- or international agency-approved medication. Typically, monotherapy dose schedules are set by determining the maximum tolerated dose (MTD) in early-stage clinical trials. The MTD (or a close variation thereon) is then promulgated to later-stage clinical trials for assessment efficacy and more detailed assessment of safety. These MTDs frequently become the established therapeutic dose upon completion of clinical testing. However, because the small molecule, systemic anti-cancer medication is contemplated for use with PV-10, a MTD is the maximal amount that would normally be used, and that amount is to be titrated downward following usual procedures.

Exemplary dosing schedules for a number of systemic anti-cancer medications that can be combined with halogenated xanthene therapy in the present invention are provided in Table A, below. It is noted that several of the medications listed below are "small molecules" as defined above, whereas others are large, proteinaceous molecules such as antibodies. They are nonetheless administered systemically.

TABLE A

Exemplary systemic immunomodulatory or targeted anticancer agents

| Systemic Agent | Typical Dose Schedule |
| --- | --- |
| adalimumab | 80 mg initial dose followed in 1 week by 40 mg every other week SQ |
| brodalumab | 210 mg subcutaneously (SC) at Weeks 0, 1, and 2, then 210 mg SC q2wk |
| certolizumab pegol | 400 mg initially and at weeks 2 and 4 followed by 200 mg every other week or 400 mg Q4 weeks maintenance SQ |
| etanercept | 50 mg twice weekly for 3 months followed by 50 mg once weekly SQ |
| golimumab | 50 mg once a month SQ |
| guselkumab | 100 mg subcutaneous injection once every 8 weeks, after starter doses at weeks 0 and 4 |
| infliximab | 5 mg/kg given as an IV induction regimen at 0, 2, and 6 weeks followed by a maintenance regimen of 5 mg/kg every 8 weeks thereafter |
| ixekizumab | 160 mg initial dose followed Q2 weeks with 80 mg until week 12 then 80 mg Q4 weeks SQ |
| sarilumab | 200 mg every 2 weeks as a subcutaneous injection |
| secukinumab | 300 mg every week for 4 weeks then 300 mg every 4 weeks SQ |
| ustekinumab | Less than 100 kg: 45 mg initially, week 4 followed by 45 mg every 12 weeks SQ More than 100 kg: 90 mg initially, week 4 followed by 90 mg every 12 weeks SQ |

TABLE A-continued

Exemplary systemic immunomodulatory or targeted anticancer agents

| Systemic Agent | Typical Dose Schedule |
| --- | --- |
| apremilast | Titrated dose over 5 days to work up to 30 mg twice daily PO |
| methotrexate | Weekly single oral, IM or IV 10 to 25 mg per week or divided 2.5 mg dose at 12 hour intervals for three doses |
| cyclosporine | Initial dose 2.5 mg/kg/day taken twice daily as divided (BID); dose titrated up to 4 mg/kg/day BID if response and laboratory abnormalities don't ensue. |
| azathioprine | Used off label for skin diseases, 1.0 mg/kg oral or IV as a single dose or twice a day, dose maximum is 2.5 mg/kg/day. |

Because of additive or synergistic effects, the combination therapies and method of treatment of the present invention generally permit use of the systemic agent at a level at or below the typical dose schedule for the systemic agent, such as those described in Table A, when used with an IV administration therapy, such as that described below. However, the dosing schedules provided in Table A provide a useful guide for beginning treatment from which dosages can be titrated to lessened amounts as seen appropriate by the physician caring for a given patient.

It is noted that a halogenated xanthene and a second cytotoxic anti-cancer agent need not be administered together nor by the same means of administration. Thus, a pill or capsule can be used to administer the second cytotoxic anti-cancer agent, while the halogenated xanthene is administered IV. Those skilled in the art are well aware of the various methods of administering anticancer agents.

A second type of second cytotoxic agent useful for combination treatment with a halogenated xanthene such as that present in PV-10 is an immune checkpoint inhibitor, that can also be viewed as a special systemic anti-cancer medication. An immune checkpoint inhibitor is a drug that binds to and blocks certain checkpoint proteins made by immune system cells such as T cells and some cancer cells. When not blocked, those proteins inhibit immune responses, helping keep immune responses in check and keeping T cells from killing cancer cells. Blocking those immune checkpoint proteins releases the "brakes" on the immune system permitting T cells to become activated and kill cancer cells.

A useful immune checkpoint inhibitor is preferably a human or humanized monoclonal antibody or binding portion thereof whose administration blocks the action of those certain proteins, thereby permitting the immune system to recognize the cancer cells as foreign and assist in eliminating those cancer cells from the body. Illustrative immune checkpoint inhibitors include the anti-CTLA-4 (cytotoxic T lymphocyte-associated antigen 4) monoclonal antibodies ipilimumab and tremelimumab that are designed to counter down-regulation of the immune system by blocking CTLA-4 activity and thus augment T-cell response against cancer. Similarly, monoclonal antibodies such as pidilizumab, nivolumab, lambrolizumab and pembrolizumab bind to PD-1 (programmed death 1) receptor to counter down-regulation of the immune system and augment T-cell responses to cancerous cells. Three antibodies that target the immune checkpoint protein ligand (PD-L1) for the PD-1 receptor (PD-L1) are atezolizumab, avelumab and durvalumab. Initial work with antibodies to the PD-1 receptor ligands, PD-L1 and PD-L2, such as BMS-936559 and MEDI4736 (durvalumab) to PD-L1, also indicate inhibition of down-regulation of the immune system and an augmented T-cell response against cancer.

Another group of antibodies with checkpoint inhibitor-like activity immunoreact with the cell surface receptor OX40 (CD134) to stimulate proliferation of memory and effector T-lymphocytes, and thereby stimulate a T-cell-mediated immune response against cancerous cells. Exemplary such humanized anti-OX40 monoclonal antibodies include those presently referred to in the literature as gsk3174998 (IgG1), pogalizumab (MOXR0916), MED10562 and the human anti-OX40 IgG2 antibody designated PF-04518600 (PF-8600).

Intact monoclonal antibodies, as well their paratope-containing portions (binding site-containing portions) such as Fab, Fab', F(ab')2 and Fv regions, as well as single-stranded peptide binding sequences can be useful as immune checkpoint protein inhibitors. Intact checkpoint inhibiting monoclonal antibodies have half-lives in a human body of about one to three weeks [e.g., Yervoy® (ipilimumab) terminal $t_{1/2}$=15.4 days; package insert 12/2013; Keytruda® (pembrolizumab) terminal $t_{1/2}$=23 days; package insert 03/2017], and single-stranded oligo or polypeptides tend to have shorter half-lives in vivo.

Because of the relatively short half-lives of the small molecule second cytotoxic anticancer agents and a halogenated xanthene medicament, both medicaments can be administered in a single composition or in separate compositions. If administered separately, it is preferred to administer both types of anticancer agent within minutes to about 3 hours of each other. More preferably, both are administered within less than one hour of the other.

As used herein, "administration" is used to mean the beginning of a treatment regimen. Thus, swallowing a tablet or other per os dosage form is the beginning of a treatment regimen, as is the time at which an IV flow is begun. When both first and second cytotoxic anticancer agents are present together in the same, single composition, administration begins when that unitary composition enters the subject's body.

Where the second cytotoxic anticancer agent is an immune checkpoint inhibitor such as a monoclonal antibody, the halogenated xanthene and the second cytotoxic anticancer agent immune checkpoint inhibitor can be administered together or one before the other, with the second cytotoxic anticancer agent immune checkpoint inhibitor being administered up to about one month prior to the halogenated xanthene. Preferably, the two cytotoxic anticancer agents are administered together or with the second cytotoxic anticancer agent immune checkpoint inhibitor being administered within a few days after the halogenated xanthene. A second cytotoxic anticancer agent immune checkpoint inhibitor can also be administered about one month after the halogenated xanthene.

Results

Results of preliminary in vitro cell culture viability assays were carried out on a panel of eleven commercially available leukemia cell lines derived from patients with either primary or relapsed pediatric leukemia that were treated with PV-10 (Table 1) and two primary leukemia samples (Table 2).

Cell viability was measured by alamar blue assay, 96 hours post-treatment. PV-10 decreased cancer cell viability in a concentration and time dependent manner in the eleven pediatric leukemia cell lines (mean $IC_{50}$ 92.8 µM), and three primary leukemia samples (mean $IC_{50}$ 122.5 µM) examined. The results show that PV-10 is cytotoxic to leukemia cell lines with a mean $IC_{50}$ value of 92.8 µM (Table 1, below) and is cytotoxic to two primary leukemia samples with a mean $IC_{50}$ value of 122.5 µM (Table 2, below).

TABLE 1*

| Cell Line | Cell Type | PV-10 $IC_{50}$ µM |
|---|---|---|
| KOPN8 | Infant ALL | 150 |
| SUPB15 | B-ALL | 129 |
| acute lymphoblastic leukemiatib = 20 | T-ALL | 121 |
| TIB-202 | AML | 118 |
| SEM | B-ALL | 99 |
| CCRF-SB | B-ALL | 88 |
| Kasumi1 | AML | 72 |
| MV4-11 | Biphenotypic | 68 |
| Molm13 | AML | 42 |
| Molt4 | T-ALL | 41 |
| Molt3 | T-ALL | 35 |
| | Mean | 92.8 |

*Half maximal inhibitory concentration ($IC_{50}$) values for pediatric leukemia cell lines treated with PV-10 for 96 hours.

TABLE 2**

| Cell Type | PV-10 $IC_{50}$ µM |
|---|---|
| T-ALL | 150 |
| Infant AML | 95 |
| Mean | 122.5 |

**Half maximal inhibitory concentration ($IC_{50}$) values for primary pediatric leukemia samples treated with PV-10 for 96 hours.

Observation of four different leukemia cell lines (Molm-13, MV4-11, SEM, TIB-202) by phase-contrast and time-lapse video microscopy indicated that PV-10 was cytotoxic and not cytostatic to the cancerous cells. Quantification of dead cells from time-lapse video microscopy experiments showed that PV-10 was cytotoxic in a cell line in a concentration-dependent manner.

At 24 hours post-treatment with 100 µM PV-10, 88% of MV4-11 cells, 69% of Molm-13 cells, 27% of TIB-202 cells and 25% of SEM cells had undergone cell death. When the concentration of PV-10 was increased to 200 µM, 100% of MV4-11 and Molm13 cells, 94% of SEM cells and 60% of TIB-202 cells had undergone cell death, 24 hours after treatment.

Additionally, observation by time-lapse video microscopy suggested that cells were dying by apoptosis, as treatment with PV-10 led to cell shrinkage. Induction of apoptosis by PV-10 was confirmed by dose and time dependent PARP cleavage, detected by western blot. [Swift et al., *Blood,* 132, No. Suppl 1: 5207 (Nov. 21, 2018).]

These studies provide first evidence in pre-clinical data for the activity and mechanisms of action of PV-10 in pediatric leukemia. These data provide the rationale for additional studies and the formulation of an early-phase clinical trial for patients with relapsed and refractory pediatric leukemia.

Methods

A panel of eleven cell lines derived from patients with either primary or relapsed pediatric leukemia (CEM-C1, CCRF-SB, Kasumi-1, KOPN8, Molm-13, Molt-3, Molt-4, MV4-11, SEM, SUP-B15 and TIB-202) and cells from three primary leukemia patient specimens (T-ALL, AML, Infant AML) were treated with increasing concentrations of PV-10 and cell viability was measured by alamar blue assay, 96 hours post-treatment. Target modulation and induction of cell death pathways were investigated by western blot, phase-contrast microscopy and time-lapse video microscopy.

Analysis of cell cycle alterations and induction of apoptosis were measured by flow cytometry. Combination studies are performed to identify anti-cancer agents that are synergistic with PV-10 and animal models of pediatric leukemia used to identify the activity of PV-10 against pediatric leukemia in vivo.

Previous Studies

Previous studies have shown that the halogenated xanthene compounds discussed previously provide results against cancerous tumor cells that are similar to those achieved with RB.

Previous Procedures

A. $1\times10^{4}$ cells/mL were injected subcutaneously into BALB/c nude mice. 2-3 Weeks were required for tumors to grow to treatable volume.

B. 20 μL to 40 μL of halogenated xanthene solutions (0.01, 0.001 or 0.1% w/v) was injected until tumor was completely infiltrated. One could see the tumor begin to turn red as the agent was injected.

C. Twenty-four hours after injection, the tumors were illuminated by laser. Laser: Coherent, Verdi 5W, 532 nm CW laser, 200 mW/cm$^2$, 100 J/cm$^2$, 4 cm$^2$ treatment zone.

D. Confirmation of Specificity by Bioassay: Color retention of the agent in the tumor 24 hours after intratumoral injection was determined by production of photodynamic damage confined to the tumor as evidenced by eschar and volume reduction after illumination. Failure of tumor to reoccur at the primary site was recorded.

E. Confirmation of Specificity by Fluorescence: Retention of compounds in the tumors 24 hours after intratumoral delivery was confirmed by visually observing fluorescence of the halogenated xanthene agent in the tumor excited by the CW laser. The 532 nm exciting wavelength was removed using a Melles Griot filter Part No. 03 FIM 008. Fluorescence of the compounds was recorded using an Olympus® digital camera (Model 0-300-L).

Results

| Compound Amount (w/w %) | Results | |
|---|---|---|
| Rose Bengal | | |
| 0.01 | 24 hours post illumination | 3/3 mice eschar production and full tumor reduction |
| | 5 days post illumination | 3/3 mice reoccurrence of tumor |
| 0.001 | 24 hours post illumination | 3/5 eschar production (1/5 partial) |
| | 5 days post illumination | 3/3 mice reoccurrence of tumor |
| Ethyl Red | | |
| 0.1 | 24 hours post illumination | 2/2 mice eschar production and full tumor reduction |
| | 3 days post illumination | 3/3 mice reoccurrence of tumor |

-continued

| Compound Amount (w/w %) | Results | |
|---|---|---|
| Red 3 | | |
| 0.1 | 24 hours post illumination | 0/3 no eschar and no tumor reduction |
| PH-12* | | |
| 0.01 | 24 hours post illumination | 3/3 mice eschar production and full tumor reduction |
| | 7 days post illumination | 0/3 mice reoccurrence of tumor |
| Ethyl-PB** | | |
| 0.01 | 24 hours post illumination | 2/2 mice eschar production and full tumor reduction |
| | 5 days post illumination | 2/2 mice reoccurrence of tumor |

*PH-12 = 2',4',5',7'-tetrabromo-4,5,6,7-tetraiodoerythrosin prepared and supplied by Molecular Probes Inc.
**Phloxine B the unesterified parent compound of Ethyl-phloxine B has been examined previously and is not retained in tumors.

Each of the patents, patent applications and articles cited herein is incorporated by reference. The articles "a" and "an" are used herein to refer to one or to more than one (i.e., to at least one) of the grammatical object of the article. Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A method of treating a mammalian subject having multiple myeloma comprising the steps of:
   (A) administering a therapeutically effective amount of a halogenated xanthene, a pharmaceutically acceptable salt or a $C_1$-$C_4$ alkyl ester thereof as a first cancer cytotoxic agent dissolved or dispersed in a pharmaceutically acceptable aqueous medium to a mammalian subject having multiple myeloma; and
   (B) maintaining said mammalian subject for a period of time sufficient to induce death of said multiple myeloma cells,
   wherein said first cancer cytotoxic agent halogenated xanthene, pharmaceutically acceptable salt or $C_1$-$C_4$ alkyl ester thereof is rose bengal disodium salt.

2. The method according to claim 1, wherein said steps are repeated.

3. The method according to claim 1, wherein said contacting is carried out in vivo in said mammalian subject.

4. The method according to claim 3, wherein said mammalian subject is selected from the group consisting of a human, an ape, a monkey, a laboratory animal, a companion animal and a food animal.

5. The method according to claim 1, wherein said administration of step (A) is carried out in conjunction with administration to said mammalian subject of a second therapeutically effective amount of a second, differently-acting cancer cytotoxic agent dissolved or dispersed in a pharmaceutically acceptable medium.

6. The method according to claim 5, wherein said second cancer cytotoxic agent is dissolved or dispersed in a pharmaceutically acceptable solid medium.

7. The method according to claim 5, wherein the pharmaceutically acceptable solid medium containing the second cancer cytotoxic agent is administered per os.

8. The method according to claim 5, wherein second cancer cytotoxic agent is a small molecule having a molecular weight of about 200 to about 1000 Da.

9. The method according to claim 5, wherein said small molecule exhibits synergy with said first cancer cytotoxic agent.

10. The method according to claim 5, wherein said second cancer cytotoxic agent is dissolved or dispersed in a pharmaceutically acceptable aqueous medium.

11. The method according to claim 10, wherein the pharmaceutically acceptable aqueous medium containing the second cancer cytotoxic agent is administered intravenously.

12. The method according to claim 11, wherein the second cancer cytotoxic agent comprises intact monoclonal antibodies or paratope-containing portions thereof.

13. The method according to claim 12, wherein said intact monoclonal antibodies or paratope-containing portions thereof are immune checkpoint protein inhibitors.

14. The method according to claim 13, wherein said immune checkpoint protein inhibitors bind to one or more proteinaceous materials selected from one or more of the group consisting of CTLA-4, PD-1, PD-L1, PD-L2, and OX40.

15. The method according to claim 5, wherein said first and said second cancer cytotoxic agents are administered simultaneously to within about 3 hours of each other.

* * * * *